(12) United States Patent
Marash et al.

(10) Patent No.: US 11,179,578 B2
(45) Date of Patent: Nov. 23, 2021

(54) PATIENT POSITIONING APPARATUS AND METHOD

(71) Applicant: P-CURE, LTD., Shilat (IL)

(72) Inventors: Michael Marash, Rishon Le'tzion (IL); Yael Braude, Rosh Ha'ayin (IL)

(73) Assignee: P-CURE, LTD., Lod (IL)

( * ) Notice: Subject to any disclaimer, the term of this patent is extended or adjusted under 35 U.S.C. 154(b) by 0 days.

(21) Appl. No.: 16/772,835

(22) PCT Filed: Dec. 20, 2018

(86) PCT No.: PCT/IL2018/051380
§ 371 (c)(1),
(2) Date: Jun. 15, 2020

(87) PCT Pub. No.: WO2019/123464
PCT Pub. Date: Jun. 27, 2019

(65) Prior Publication Data
US 2020/0353289 A1    Nov. 12, 2020

Related U.S. Application Data

(60) Provisional application No. 62/608,578, filed on Dec. 21, 2017.

(51) Int. Cl.
*A61N 5/10* (2006.01)
(52) U.S. Cl.
CPC .......... *A61N 5/1049* (2013.01); *A61N 5/103* (2013.01); *A61N 5/1069* (2013.01); *A61N 5/1078* (2013.01)
(58) Field of Classification Search
None
See application file for complete search history.

(56) References Cited

U.S. PATENT DOCUMENTS

| 3,585,386 | A |   | 6/1971 | Horton |   |
|---|---|---|---|---|---|
| 5,921,696 | A | * | 7/1999 | Gillotti | A47C 9/005 403/109.1 |

(Continued)

FOREIGN PATENT DOCUMENTS

| CN | 1913802 A | 2/2007 |
|---|---|---|
| CN | 101686893 A | 3/2010 |

(Continued)

OTHER PUBLICATIONS

International search report for PCT application PCT/IL2018/051380, issued by the USPTO dated Apr. 8, 2019.
(Continued)

*Primary Examiner* — Hoon K Song
(74) *Attorney, Agent, or Firm* — The Roy Gross Law Firm, LLC; Roy Gross (57) ABSTRACT

A patient positioning method constituted of: rotating a pelvis support member about a first axis; rotating the pelvis support member about a second axis, between a first position where the pelvis of a patient is supported by a first face of the pelvis support member and a second position where the pelvis of the patient is supported by a second face of the pelvis support member, the rotation being at least 180 degrees about the second rotation axis; and adjusting an angle between the pelvis support member and a torso support member between a first angle where the torso support member supports the torso of the patient when the pelvis is supported by the first face of the pelvis support member and a second angle where the torso support member supports the torso of the patient when the pelvis is supported by the second face of the pelvis support member.

8 Claims, 7 Drawing Sheets

(56) References Cited

U.S. PATENT DOCUMENTS

| | | | |
|---|---|---|---|
| 6,155,994 | A | 12/2000 | Hubbard et al. |
| 7,010,369 | B2 | 3/2006 | Borders et al. |
| 10,517,404 | B2 * | 12/2019 | Hopper .................. A47C 7/543 |
| 2005/0234327 | A1 | 10/2005 | Saracen et al. |
| 2007/0052275 | A1 * | 3/2007 | Ghilzai .................... A47C 1/11 |
| | | | 297/423.12 |
| 2013/0307298 | A1 * | 11/2013 | Meiki ...................... A61G 7/16 |
| | | | 297/68 |
| 2021/0077043 | A1 * | 3/2021 | Naylor ................. A61B 6/4007 |
| 2021/0113162 | A1 * | 4/2021 | Schmotz .............. A61B 6/0487 |
| 2021/0140395 | A1 * | 5/2021 | Lim ..................... F02M 31/135 |

FOREIGN PATENT DOCUMENTS

| | | |
|---|---|---|
| CN | 102119586 A | 7/2011 |
| CN | 106535829 A | 3/2017 |
| CN | 206261784 U | 6/2017 |
| WO | 2014172700 A1 | 10/2014 |

OTHER PUBLICATIONS

Written opinion for the international search report for PCT application PCT/IL2018/051380, issued by the USPTO dated Apr. 8, 2019.

* cited by examiner

PATIENT POSITIONING APPARATUS AND METHOD

CROSS-REFERENCE TO RELATED APPLICATIONS

The present application claims priority from U.S. provisional patent application Ser. 62/608,578, filed Dec. 21, 2017 and entitled "PATIENT POSITIONING APPARATUS AND METHOD", the entire contents of which are incorporated herein by reference.

TECHNICAL FIELD

Theinvention relates generally to the field of teletherapy and in particular to a patient positioning apparatus and method.

BACKGROUND

Teletherapy is defined as a treatment methodology in which an irradiation source is at a distance from the body to be treated. X-rays and electron beams have long been used in teletherapy to treat various cancers, and more recently the use of heavy particles, such as protons, in teletherapy has increased.

The radiation can be focused to a target volume of variable penetration depth. In this way the dose profile can be matched closely to the target volume with a high precision. In order to ensure complete irradiation of the target growth, a plurality of beams arriving at the embedded growth from several different directions is preferred. The point at which the plurality of beams intersects, whether they are beamed sequentially or simultaneously, is termed the isocenter, and to maximize biological effectiveness the isocenter must be precisely collocated with the target growth.

Irradiation treatment is performed on a target tissue in a well-defined process. In a first stage, known as the treatment planning stage, the target tissue is imaged and a treatment plan comprising dosage, patient position, and irradiation angles are defined. Furthermore, placement markers are defined, so as to ensure that subsequent irradiation sessions are properly targeted. Irradiation is then performed, responsive to the developed treatment plan, at a plurality of treatment sessions over a period of time, each session being known as a fraction. At each such fraction, care must be taken to ensure proper patient positioning, responsive to the placement markers, so as to avoid damage to organs in vicinity of the target tissue. Positioning of the patient responsive to the markers is performed based on visualization of the patient, responsive to the defined markers.

Particularly, during each fraction, the patient is positioned on a patient support member, such as a bed, in a setup position. The setup position is identical to the patient position during the imaging of the treatment planning stage, except that is in the treatment room and the center of the growth mass is positioned at the isocenter of the irradiation source. The setup position of the patient is typically verified by imaging and/or positioning devices.

U.S. Pat. No. 7,847,275, granted Dec. 7, 2010 to Lifshitz et al., the entire contents of which are incorporated herein by reference, is addressed to a teletherapy positioning apparatus which is adapted to translate a patient support member along any of three orthogonal axes and rotate the patient support member at least 180 degrees about each of three axes so as to position the patient support member with respect to a fixed treatment beam, thus allowing a patient who is lying down to be treated at any desired angle. Although this allows treatment at a variety of angles, it is limited to a flat patient support member where the patient is lying down.

SUMMARY OF THE INVENTION

Accordingly, it is a principal object of the present invention to overcome disadvantages of prior art methods and arrangements of teletherapy. This is provided in the present invention by a patient position apparatus comprising: a control circuitry; a first rotation mechanism exhibiting a first rotation axis extending therethrough; a second rotation mechanism exhibiting a second rotation axis extending therethrough, the second rotation axis generally orthogonal to the first rotation axis, the second rotation mechanism coupled to the first rotation mechanism so as to rotate about the first rotation axis responsive to rotation of the first rotation mechanism; a pelvis support member generally defining a first plane and exhibiting a first face and a second face opposing the first face, the pelvis support member coupled to the second rotation mechanism so as to rotate the first plane about the second rotation axis; and a torso support member generally defining a second plane and coupled to the pelvis support member, the second plane at a predetermined adjustable angle to the first plane, the torso support member arranged to support the torso of the patient when the pelvis of the patient is supported by the pelvis support member, the control circuitry arranged to: control the first rotation mechanism to rotate the pelvis support member about the first rotation axis, and control the second rotation mechanism to rotate the pelvis support member between a first position where the pelvis of the patient is supported by the first face of the pelvis support member and a second position where the pelvis of the patient is supported by the second face of the pelvis support member, the rotation between the first position and the second position being at least 180 degrees about the second rotation axis, wherein the angle between the second plane and the first plane is adjusted between a first angle where the torso support member supports the torso of the patient when the pelvis of the patient is supported by the first face of the pelvis support member and a second angle where the torso support member supports the torso of the patient when the pelvis of the patient is supported by the second face of the pelvis support member.

In one embodiment, the control circuitry is further arranged to control the second rotation mechanism to rotate the pelvis support member to any of a plurality of predetermined additional positions between the first position and the second position. In another embodiment, the predetermined adjustable angle is selected such that a distance between the second plane defined by the torso support member and knees of the patient is less than an inner diameter of a 3 dimensional imager arranged for imaging the patient when the patient is supported by the pelvis support member and the torso support member.

In one embodiment, the patient position apparatus further comprises a third rotation mechanism exhibiting a third rotation axis extending therethrough, the third rotational axis generally parallel to the second rotation axis, the third rotation mechanism coupled to the first rotation mechanism so as to rotate about the first rotation axis responsive to rotation of the first rotation mechanism, the torso support member coupled to the third rotation mechanism so as to rotate the second plane about the third rotation axis, wherein the adjustment of the angle is responsive to the rotation of the third rotation mechanism.

In one independent embodiment, a patient positioning method is provided, the method comprising: rotating a pelvis support member about a first rotation axis; rotating the pelvis support member about a second rotation axis, between a first position where the pelvis of a patient is supported by a first face of the pelvis support member and a second position where the pelvis of the patient is supported by a second face of the pelvis support member, the second face opposing the first face, the rotation between the first position and the second position being at least 180 degrees about the second rotation axis, the second rotation axis generally orthogonal to the first rotation axis; and adjusting a predetermined angle between a first plane defined by the pelvis support member and a second plane defined by a torso support member arranged to support the torso of the patient, the adjustment of the angle being between a first angle where the torso support member supports the torso of the patient when the pelvis of the patient is supported by the first face of the pelvis support member and a second angle where the torso support member supports the torso of the patient when the pelvis of the patient is supported by the second face of the pelvis support member.

In one embodiment, the method further comprises rotating the pelvis support member to any of a plurality of predetermined additional positions between the first position and the second position. In another embodiment, the predetermined adjustable angle is selected such that a distance between the second plane defined by the torso support member and knees of the patient is less than an inner diameter of a 3 dimensional imager arranged for imaging the patient when the patient is supported by the pelvis support member and the torso support member.

In one embodiment, the method further comprises rotating the second plane about a third rotation axis, the third rotation axis generally parallel to the second rotation axis, wherein the adjustment of the angle is responsive to the rotation about the third rotation axis.

Additional features and advantages of the invention will become apparent from the following drawings and description.

BRIEF DESCRIPTION OF THE DRAWINGS

For a better understanding of the invention and to show how the same may be carried into effect, reference will now be made, purely by way of example, to the accompanying drawings in which like numerals designate corresponding elements or sections throughout.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings.

DETAILED DESCRIPTION OF THE PREFERRED EMBODIMENTS

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

FIGS. 1A-1K illustrate various high level views of a patient position apparatus 10. Patient position apparatus 10 comprises: a control circuitry 20 comprising a user input circuitry 22 and a processor 24; a rotation mechanism 30 exhibiting a rotation axis 35 extending therethrough; a rotation axis 40 exhibiting a first end 41 and a second end 42 opposing first end 41, and a rotation axis 45 extending therethrough; a pelvis support member 50 generally defining a plane 51 and exhibiting a first face 52 and a second face 53 opposing first face 52; and a torso support member 60 generally defining a plane 61.

In one embodiment, as illustrated, rotation mechanism 30 comprises: a base 31 exhibiting a first face 32 and a second face 33, second face 33 opposing first face 32; and an extension member 36 extending from first face 32 of base 31 at a predetermined acute angle. In one further non-limiting embodiment, base 31 is generally circular shaped. In another further non-limiting embodiment, extension member 36 comprises a first arm 37A and a second arm 37B, second arm 37B generally parallel to first arm 37A. Rotation axis 35 extends through first face 32 and second face 33 of base 31, preferably through the center of base 31. In another embodiment, base 31 of rotation mechanism 30 is coupled to a dedicated motor (not shown), in communication with control circuitry 20 and arranged to rotate rotation mechanism 30 about rotation axis 35, i.e. arranged to swivel rotation mechanism 30.

In one embodiment, rotation mechanism 30 is coupled to a robotic arm 70. In one embodiment, robotic arm comprises: a rotation mechanism 80 exhibiting a rotation axis 85; a rotation mechanism 90 exhibiting a rotation axis 95; a rotation mechanism 100 exhibiting a rotation axis 105; and a rotation mechanism 110 exhibiting a rotation axis 115, each of rotation mechanism 80, 90, 100 and 110 preferably comprising a dedicated motor (not shown) in communication with control circuitry 20. In one further embodiment, rotation axis 85 is generally orthogonal to rotation axis 35 and rotation axis 95 is generally orthogonal to rotation axis 85. Rotation axis 105 is generally orthogonal to rotation axis 95 and generally parallel to rotation axis 85. Rotation axis 115 is generally orthogonal to rotation axis 95. Due to the positioning of rotation axes 85, 95, 105 and 115, robotic arm 70 provides movement with 4 degrees of freedom.

First end 41 of rotation mechanism 40 is coupled to extension member 36 such that a rotation of rotation mechanism 30 about rotation axis 35 further rotates rotation mechanism 40 about rotation axis 35, due to the mechanical connection therebetween. Specifically, the rotation of rotation mechanism 40 about rotation axis 35 is inherent to the rotation of rotation mechanism 30 about rotation axis 35 because they are connected to each other. In one embodiment, first end 41 of rotation mechanism 40 is coupled between first arm 37A and second arm 37B. Preferably, rotation axis 45 is generally orthogonal to rotation axis 35 of rotation mechanism 30. Further preferably, rotation axis 45 intersects the connection of rotation mechanism 40 and rotation mechanism 30.

In one embodiment, pelvis support member 50 is generally rectangular shaped. Pelvis support member 50 is coupled to rotation mechanism 40 such that a rotation of rotation mechanism 30 about rotation axis 35 further rotates plane 51 of pelvis support member 50 about rotation axis 35, due to the mechanical connection of pelvis support member 50 to rotation mechanism 40. Specifically, the rotation of plane 51 about rotation axis 35 is inherent to the rotation of rotation mechanism 30 about rotation axis 35 because they are connected to each other. Additionally, a rotation of rotation mechanism 40 about rotation axis 45 further rotates planed 51 about rotation axis 45, due to the mechanical connection therebetween. Specifically, the rotation of plane 51 about rotation axis 45 is inherent to the rotation of rotation mechanism 40 about rotation axis 45 because they are connected to each other.

Torso support member 60 is coupled to pelvis support member 50. In one embodiment, torso support member 60 is directly coupled to pelvis support member 50. In another embodiment, torso support member 60 is coupled to pelvis support member 50 via rotation mechanism 30 and/or rotation mechanism 40. Plane 61 of torso support member 60 exhibits a predetermined adjustable angle with plane 51 of pelvis support member 50. In one embodiment, torso support member 60 is removed from pelvis support member 50 by a predetermined distance.

In one embodiment, torso support member 60 is detachable, such that the angle between plane 51 and plane 61 is adjusted by detaching torso support member 60 from its connection in relation to pelvis support member 50 and reattaching torso support member 60 in relation to pelvis support member 50 in a different configuration. In another embodiment, as illustrated in FIG. 1K, a rotation mechanism 120 is further provided arranged to rotate about rotation axis 125, rotation mechanism 120 arranged to rotate torso support member 60 about rotation axis 125 between a first position and a second position. In one embodiment, rotation axis 125 is generally parallel to rotation axis 45. In the first position, torso support member 60 faces first face 52 of pelvis support member 50. In the second position, torso support member 60 faces second face 53 of pelvis support member 50. It is noted that the adjustable angle between planes 51 and 61 is measured between torso support member 60 and first face 52 of pelvis support member 50.

A patient 130 is supported by patient position apparatus 10 such that the pelvis of patient 130 is supported by pelvis support member 50 and the torso of patient 130 is supported by torso support member 60, as will be described below.

In operation, responsive to a user input at user input circuitry 22 of control circuitry 204, processor 24 controls rotational mechanisms 80, 90, 100 and 110 of robotic arm 70 to rotate about the respective rotation axes 85, 95, 100 and 105 by respective angles in accordance with the received user input.

Additionally, processor 24 controls rotational mechanism 30 to rotate pelvis support member 50 about rotation axis 35 by a respective angle in accordance with the received user input.

Furthermore, processor 24 controls rotational mechanism 40 to rotate pelvis support member 50 about rotation axis 45 by a respective angle in accordance with the received user input. Particularly, processor 24 control rotational mechanism 40 to rotate pelvis support member 40 anywhere between a first position and a second position, i.e. from a first of a plurality of predetermined points between the first position and the second position to a second of the plurality of predetermined points. In the first position, the pelvis of patient 130 is supported by first face 52 of pelvis support member 50 and in the second position the pelvis of patient 130 is supported by second face 53 of pelvis support member 50. The rotation between the first position and the second position is at least 180 degrees about rotation axis 45.

Particularly, in one embodiment, in the first position first face 52 of pelvis support member 50 generally faces the ceiling 140 of a treatment room and second face 53 generally faces the floor 150 of the treatment room. In the second position, first face 52 generally faces floor 150 of the treatment room and second face 53 generally faces ceiling 140 of the treatment room. In one embodiment, when moving between the first and second positions, pelvis support member 50 is further rotated by rotation mechanism 30 about rotation axis 35 so the legs of patient won't get hit by robotic arm 70.

Furthermore, the angle between plane 61 of torso support member 60 and plane 51 of pelvis support member 50 is adjusted between a first predetermined angle and a second predetermined angle. When exhibiting the first predetermined angle therebetween, torso support member 60 supports the torso of patient 130 when the pelvis of patient 130 is supported by first face 52 of pelvis support member 50. When exhibiting the second predetermined angle therebetween, torso support member 60 supports the torso of patient 130 when the pelvis of patient 130 is supported by second face 53 of pelvis support member 50.

Figure 1A:
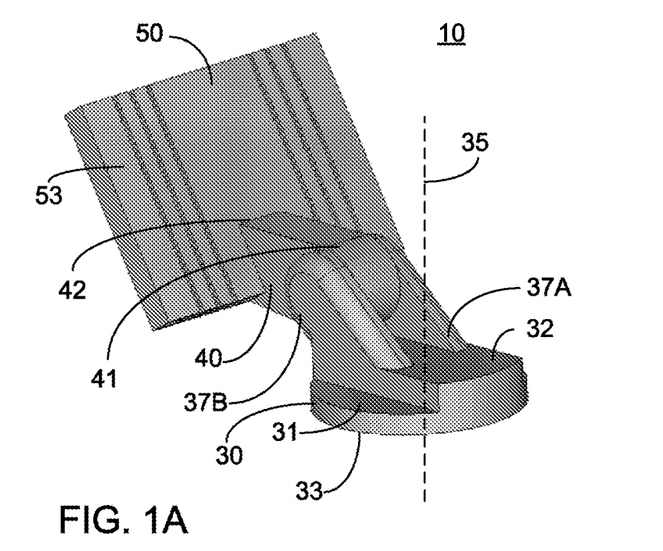
FIGS. 1A-1K illustrate various high level views of a patient position apparatus, in accordance with certain embodiments.
Figure 1B:
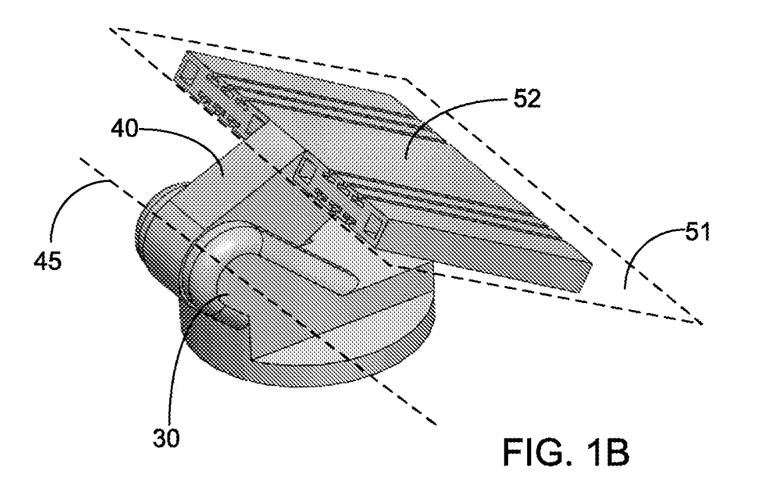
Figure 1C:
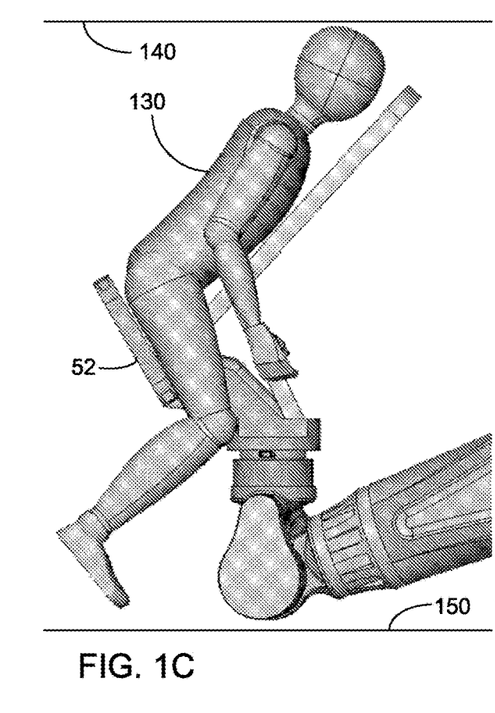
Figure 1D:
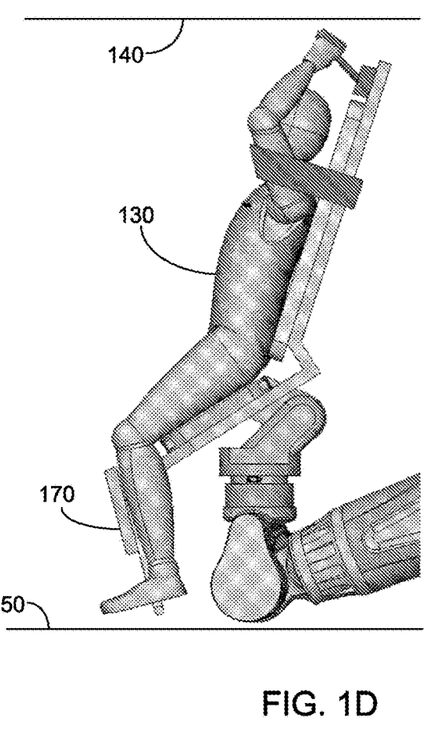
Figure 1E:
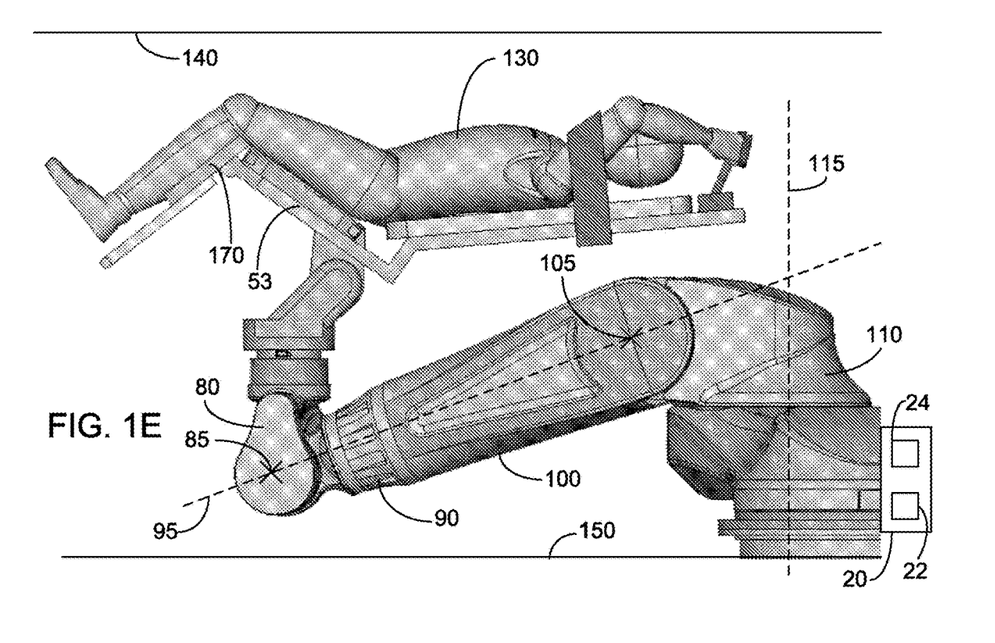

The first position of pelvis support member 50 allows for patient 130 to be supported in a semi-standing position, as illustrated in FIG. 1C, where patient 130 faces ceiling 140 of the treatment room. The second position of pelvis support member 50 allows for patient 130 to be supported in a tilted forward position, as illustrated in FIG. 1D, where patient 130 faces floor 150 of the treatment room. Additionally, the plurality of additional positions between the first and second positions allow for a variety of positions for patient 130, such as a supine position, as illustrated in FIG. 1E. As described above, the position of patient 130 is further adjusted responsive to robotic arm 70. As a result, patient 130 can be moved with 6 degrees of freedom by being rotated about any of rotation axes 35, 45, 85, 95, 105 and 115.

Figure 1F:
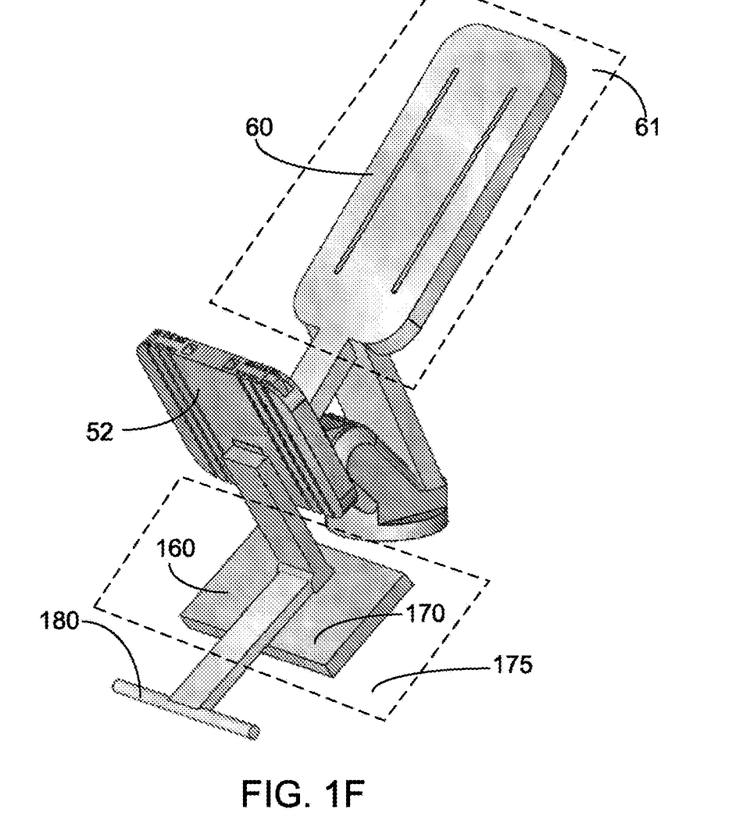
Figure 1G:
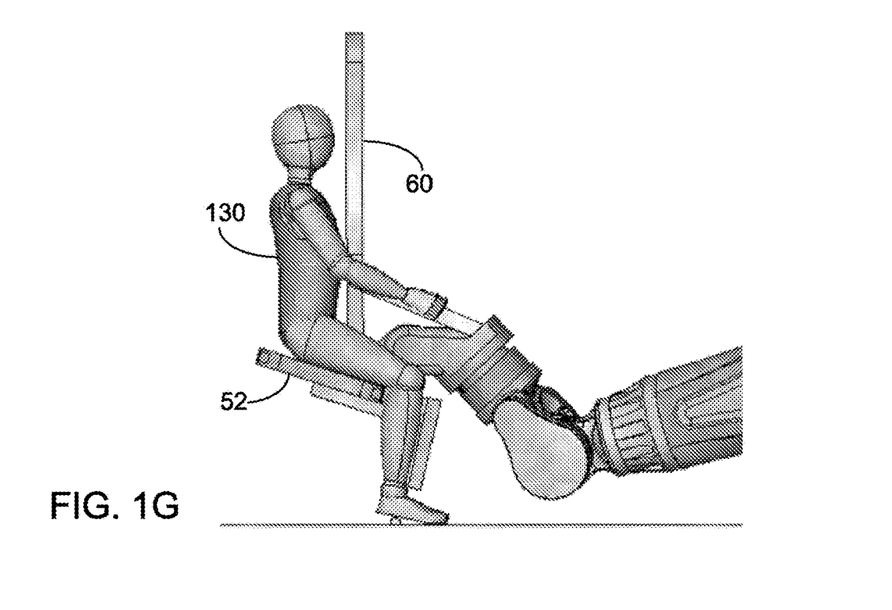
Figure 1H:
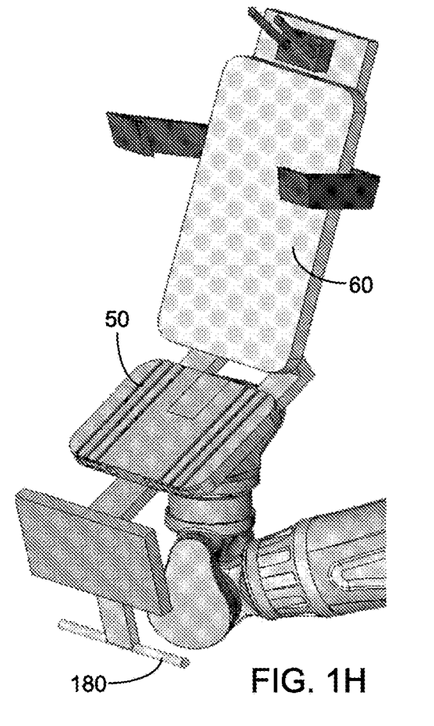
Figure 1I:
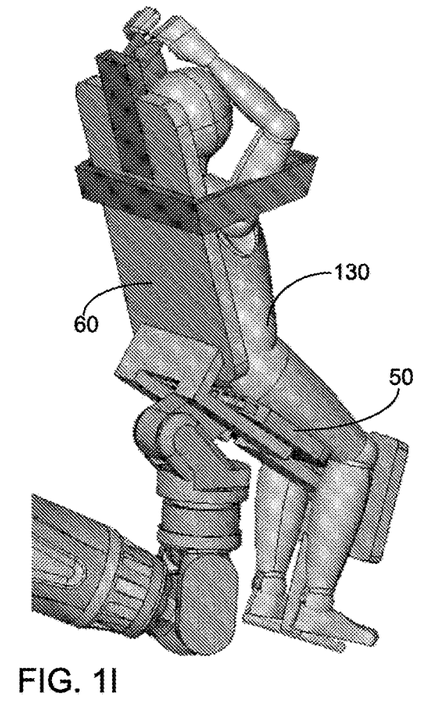

In one embodiment, as illustrated in FIGS. 1F-1I, patient position apparatus 10 further comprises a leg support 160. Leg support 160 comprises a shin support 170 and a foot rest 180. In one further embodiment, shin support 170 defines a plane 175, plane 175 generally orthogonal to plane 51 of pelvis support member 50, shin support 170 coupled to pelvis support member 50. Foot rest 180 extends from shin support 170 along plane 175. The shins of patient 130 rest against shin support 170 and the feet of patient 130 rest against foot rest 180. In one embodiment, leg support 160 is detachable from pelvis support member 50, such that when pelvis support member 50 is positioned in the second position, leg support 160 is attached to first face 52 of pelvis support member 50, as illustrated in FIGS. 1F-1G. Additionally, when pelvis support member 50 is positioned in the first position, leg support 160 is attached to second face 53 of pelvis support member 50, as illustrated in FIGS. 1H-1I.

Figure 1J:
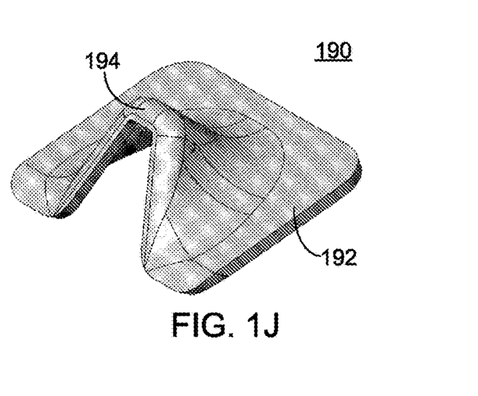
Figure 1K:
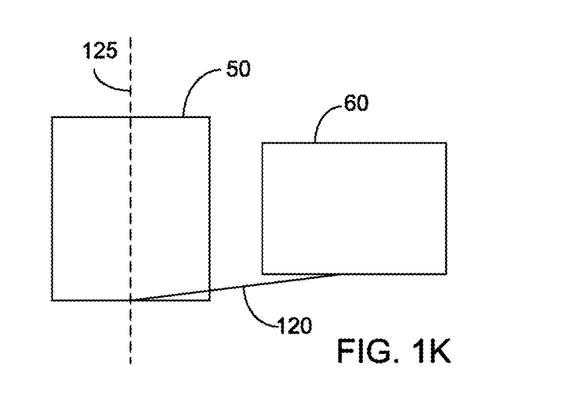

In another embodiment, patient support apparatus 10 further comprises a patient securing member 190, illustrated in FIG. 1J. Patient securing member 190 exhibits a base 192 which rises in the center to an apex 194. Base 192 is secured to pelvis support member 50 and patient 130 sits thereon, apex 194 preventing patient 130 from sliding off when pelvis support member 50 is on an angle and patient 130 is facing floor 150 of the treatment room.

It is noted that the rotations of robotic arm 70 and pelvis support member 50 can be performed before or after patient 130 is positioned on pelvis support member 50. Alternately, part of the rotations can be performed before patient 130 is positioned on pelvis support member 50 and the rest can be performed after, as desired.

Figure 2A:
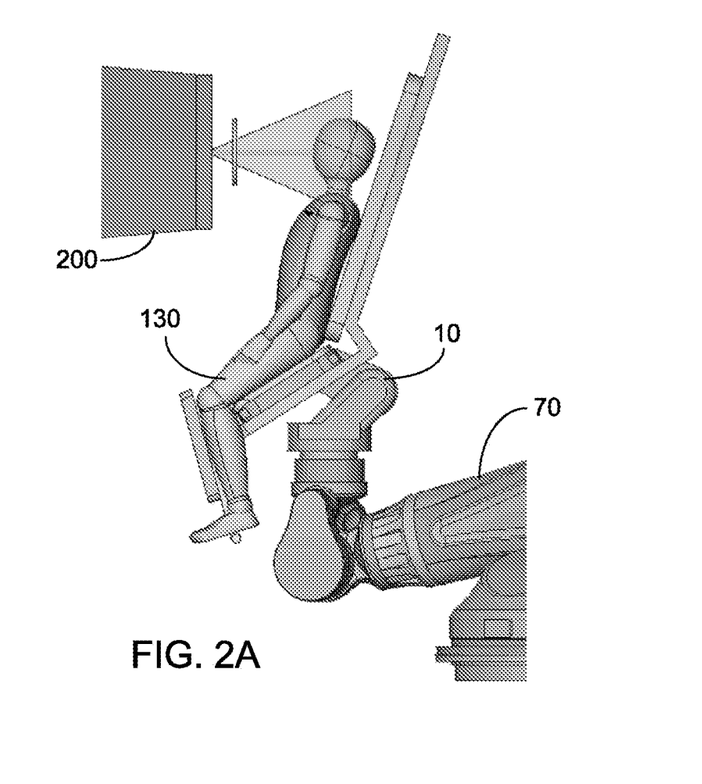
FIGS. 2A-2B illustrate positioning of a patient supported by the patient position apparatus of FIGS. 1A-1K in relation to a fixed beam radiation source.
Figure 2B:
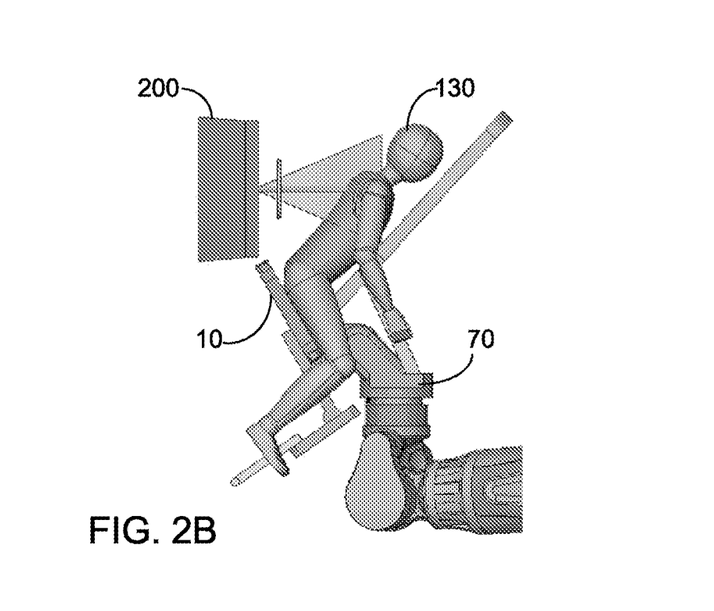

As illustrated in FIGS. 2A-2B, patient 130 can be positioned in any desired position for radiation therapy from a fixed radiation source 200. Particularly, as described above, robotic arm 70 and patient position apparatus 10 are rotated, in six degrees of freedom, to achieve any desired position of patient 130 in relation to the radiation beam output by fixed radiation source 200.

Figure 3A:
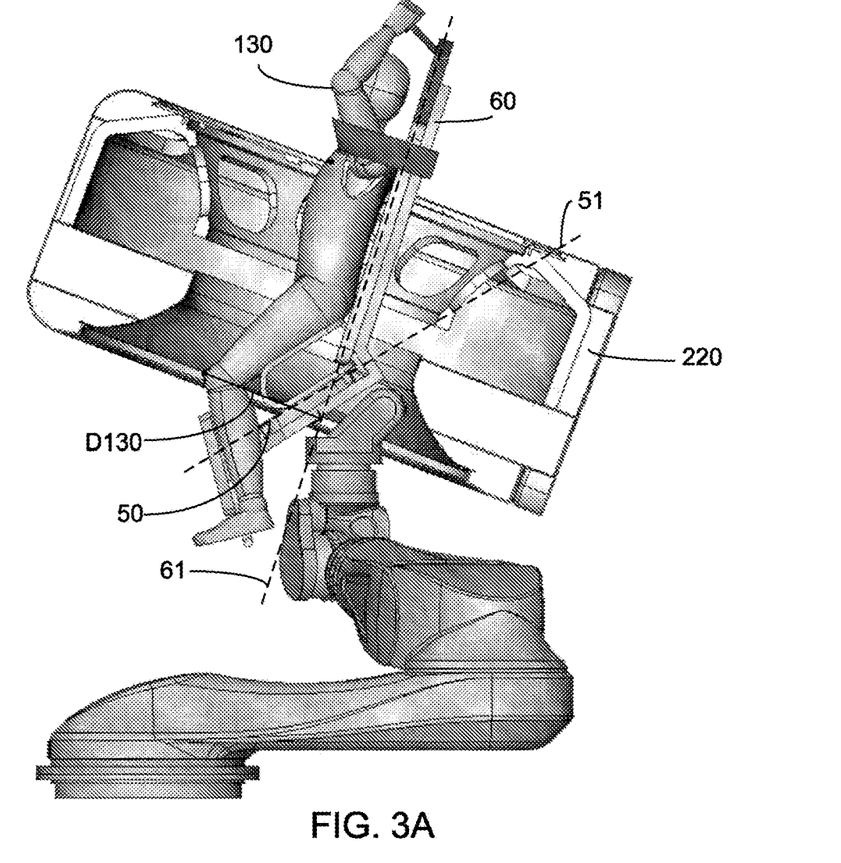
FIGS. 3A-3B illustrate positioning of a patient supported by the patient position apparatus of FIGS. 1A-1K in relation to a 3 dimensional imager.
Figure 3B:
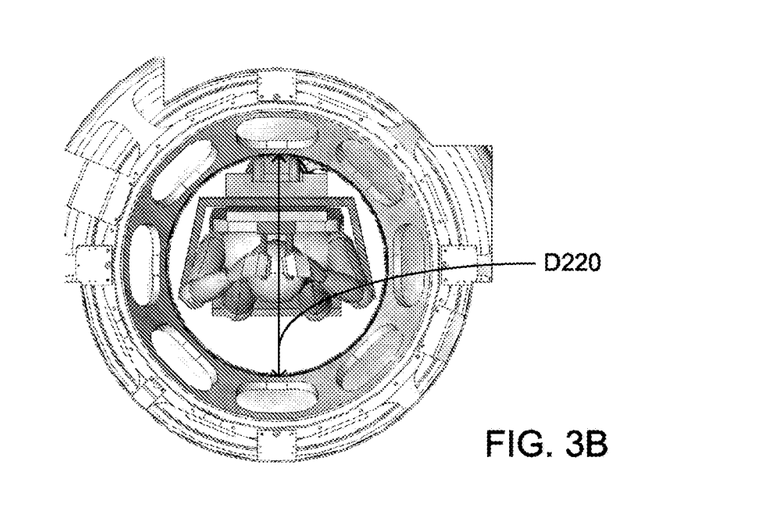

As illustrated in FIGS. 3A-3B, patient 130 can further be positioned for 3 dimensional (3D) imaging. In one embodiment, the predetermined adjustable angle described above between plane 51 of pelvis support member 50 and plane 61 of torso support member is selected such that the distance between plane 61 and the knees of patient 130, denoted D130, is less than an inner diameter 210 of a 3D imager 220, denoted D220. Particularly, 3D imager 220 is arranged to image patient 130 when patient 130 is supported by pelvis support member 50 and torso support member 60, as described above. 3D imager 220 is moved along patient 130 for imaging. By positioning patient 130 in a semi-standing position, as illustrated in FIG. 3A, distance D is reduced to less than distance D220 and the movement of 3D imager 220 is not impeded by patient 130's knees. Although 3D imager 220 is illustrated as a circular computed tomography (CT) imager, this is not meant to be limiting in any way. In another embodiment, 3D imager 220 can be any suitable 3D imager, such as a cone beam CT imager, a magnetic resonance imager (MRI) and a positron emission tomography (PET) imager, without limitation.

Figure 4:
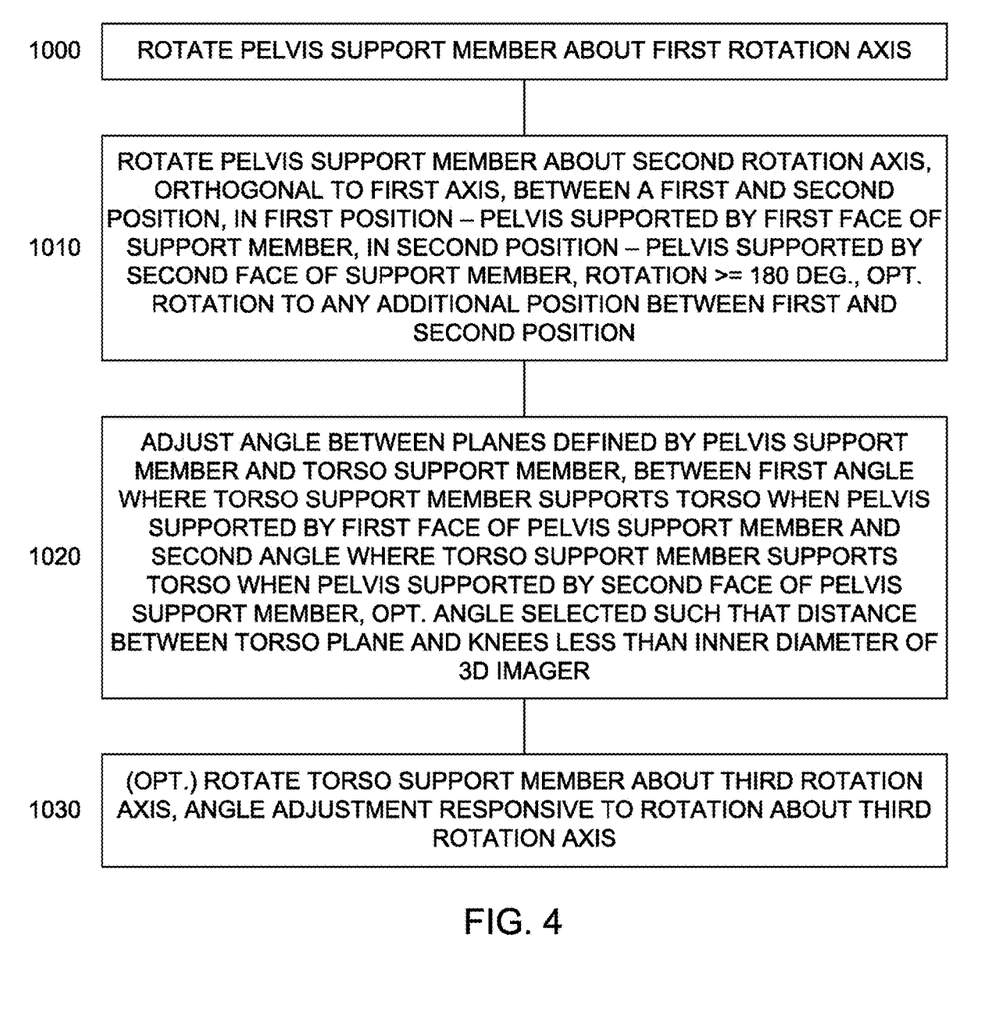
FIG. 4 illustrates a high level flow chart of a method of patient positioning in accordance with certain embodiments.

FIG. 4 illustrates a high level flow chart of a patient positioning method, in accordance with certain embodiments. In stage 1000, a pelvis support member is rotated about a first rotation axis. The pelvis support member support the pelvis of a patient. In stage 1010, the pelvis support member of stage 1000 is rotated about a second rotation axis between a first position and a second position. The second rotation axis is generally orthogonal to the first rotation axis of stage 1000.

In the first position, the pelvis of the patient of stage 1000 is supported by a first face of the pelvis support member. In the second position, the pelvis of the patient is supported by a second face of the pelvis support member, the second face opposing the first face. The rotation between the first position and the second position is at least 180 degrees about the second rotation axis.

Optionally, the pelvis support member is rotated to any of a plurality of predetermined additional positions between the first position and the second position.

In stage 1020, a predetermined angle between a first plane defined by the pelvis support member of stage 1000 and a second plane defined by a torso support member arranged to support the torso of the patient is adjusted. The adjustment of the angle is between a first angle where the torso support member supports the torso of the patient when the pelvis of the patient is supported by the first face of the pelvis support member and a second angle where the torso support member supports the torso of the patient when the pelvis of the patient is supported by the second face of the pelvis support member.

Optionally, the predetermined adjustable angle is selected such that a distance between the second plane defined by the torso support member and knees of the patient is less than an inner diameter of a 3D imager arranged for imaging the patient when the patient is supported by the pelvis support member and the torso support member.

In optional stage 1030, the second plane defined by the torso support member is rotated about a third rotation axis. The third rotation axis is generally parallel to the second rotation axis of stage 1010. The angle adjustment of stage 1020 is responsive to said rotation about the third rotation axis. As described above, in one embodiment the torso support member is rotated to the opposite side of the pelvis support member.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

Unless otherwise defined, all technical and scientific terms used herein have the same meanings as are commonly understood by one of ordinary skill in the art to which this invention belongs. Although methods similar or equivalent to those described herein can be used in the practice or testing of the present invention, suitable methods are described herein.

All publications, patent applications, patents, and other references mentioned herein are incorporated by reference in their entirety. In case of conflict, the patent specification, including definitions, will prevail. In addition, the materials, methods, and examples are illustrative only and not intended to be limiting.

The terms "include", "comprise" and "have" and their conjugates as used herein mean "including but not necessarily limited to".

It will be appreciated by persons skilled in the art that the present invention is not limited to what has been particularly shown and described hereinabove. Rather the scope of the present invention is defined by the appended claims and includes both combinations and sub-combinations of the various features described hereinabove as well as variations and modifications thereof, which would occur to persons skilled in the art upon reading the foregoing description.

The invention claimed is:

1. A patient position apparatus comprising:
   a control circuitry;
   a first rotation mechanism exhibiting a first rotation axis extending therethrough;
   a second rotation mechanism exhibiting a second rotation axis extending therethrough, said second rotation axis generally orthogonal to said first rotation axis, said second rotation mechanism coupled to said first rotation mechanism so as to rotate about said first rotation axis responsive to rotation of said first rotation mechanism;
   a pelvis support member generally defining a first plane and exhibiting a first face and a second face opposing said first face, said pelvis support member coupled to said second rotation mechanism so as to rotate said first plane about said second rotation axis; and a torso support member generally defining a second plane and coupled to said pelvis support member, said second plane at a predetermined adjustable angle to said first plane, said torso support member arranged to support the torso of the patient when the pelvis of the patient is supported by said pelvis support member, said control circuitry arranged to:
control said first rotation mechanism to rotate said pelvis support member about said first rotation axis, and
control said second rotation mechanism to rotate said pelvis support member between a first position where the pelvis of the patient is supported by said first face of said pelvis support member and a second position where the pelvis of the patient is supported by said second face of said pelvis support member, said rotation between said first position and said second position being at least 180 degrees about said second rotation axis, wherein said angle between said second plane and said first plane is adjusted between a first angle where said torso support member supports the torso of the patient when the pelvis of the patient is supported by said first face of said pelvis support member and a second angle where said torso support member supports the torso of the patient when the pelvis of the patient is supported by said second face of said pelvis support member.

2. The patient position apparatus of claim 1, wherein said control circuitry is further arranged to control said second rotation mechanism to rotate said pelvis support member to any of a plurality of predetermined additional positions between said first position and said second position.

3. The patient position apparatus of claim 1, wherein said predetermined adjustable angle is selected such that a distance between said second plane defined by said torso support member and knees of the patient is less than an inner diameter of a 3 dimensional imager arranged for imaging the patient when the patient is supported by said pelvis support member and said torso support member.

4. The patient position apparatus of claim 1, further comprising a third rotation mechanism exhibiting a third rotation axis extending therethrough, said third rotational axis generally parallel to said second rotation axis, said third rotation mechanism coupled to said first rotation mechanism so as to rotate about said first rotation axis responsive to rotation of said first rotation mechanism, said torso support member coupled to said third rotation mechanism so as to rotate said second plane about said third rotation axis, wherein said adjustment of said angle is responsive to said rotation of said third rotation mechanism.

5. A patient positioning method, the method comprising:
rotating a pelvis support member about a first rotation axis;
rotating the pelvis support member about a second rotation axis, between a first position where the pelvis of a patient is supported by a first face of the pelvis support member and a second position where the pelvis of the patient is supported by a second face of the pelvis support member, the second face opposing the first face, said rotation between said first position and said second position being at least 180 degrees about said second rotation axis, said second rotation axis generally orthogonal to said first rotation axis; and
adjusting a predetermined angle between a first plane defined by the pelvis support member and a second plane defined by a torso support member arranged to support the torso of the patient, said adjustment of said angle being between a first angle where the torso support member supports the torso of the patient when the pelvis of the patient is supported by the first face of the pelvis support member and a second angle where the torso support member supports the torso of the patient when the pelvis of the patient is supported by the second face of the pelvis support member.

6. The method of claim 5, further comprising rotating the pelvis support member to any of a plurality of predetermined additional positions between said first position and said second position.

7. The method of claim 5, wherein said predetermined adjustable angle is selected such that a distance between the second plane defined by the torso support member and knees of the patient is less than an inner diameter of a 3 dimensional imager arranged for imaging the patient when the patient is supported by the pelvis support member and the torso support member.

8. The method of claim 5, further comprising rotating the second plane about a third rotation axis, said third rotation axis generally parallel to said second rotation axis, wherein said adjustment of said angle is responsive to said rotation about said third rotation axis.

* * * * *